(12) United States Patent
Zaidel

(10) Patent No.: US 9,918,926 B2
(45) Date of Patent: *Mar. 20, 2018

(54) ORAL CARE COMPOSITIONS AND METHODS

(71) Applicant: COLGATE-PALMOLIVE COMPANY, New York, NY (US)

(72) Inventor: Lynette A. Zaidel, Cranford, NJ (US)

(73) Assignee: Colgate-Palmolive Company, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/106,456

(22) PCT Filed: Dec. 20, 2013

(86) PCT No.: PCT/US2013/076885
§ 371 (c)(1),
(2) Date: Jun. 20, 2016

(87) PCT Pub. No.: WO2015/094332
PCT Pub. Date: Jun. 25, 2015

(65) Prior Publication Data
US 2016/0331668 A1    Nov. 17, 2016

(51) Int. Cl.
*A61K 8/81* (2006.01)
*A61K 8/24* (2006.01)
*A61K 8/27* (2006.01)
*A61Q 11/00* (2006.01)
*C08L 43/02* (2006.01)

(52) U.S. Cl.
CPC .............. *A61K 8/8152* (2013.01); *A61K 8/24* (2013.01); *A61K 8/27* (2013.01); *A61K 8/8147* (2013.01); *A61K 8/8164* (2013.01); *A61Q 11/00* (2013.01); *C08L 43/02* (2013.01); *A61K 2800/5424* (2013.01); *A61K 2800/594* (2013.01)

(58) Field of Classification Search
None
See application file for complete search history.

(56) References Cited

U.S. PATENT DOCUMENTS

| 5,425,953 A | 6/1995 | Sintov et al. |
| 5,766,574 A | 6/1998 | Christina-Beck et al. |
| 2004/0208834 A1* | 10/2004 | Koudate .............. A61K 8/8135 424/49 |
| 2011/0152083 A1* | 6/2011 | Lu ........................... C09D 4/00 504/101 |

FOREIGN PATENT DOCUMENTS

JP    2007/284609 A    11/2015

OTHER PUBLICATIONS

"Innovative Ingredients for Oral Care", Ashland, Brochure, 2013, 13 pages, Date Accessed: Aug. 24, 2016 (http://www.ashland.com/Ashland/Static/Documents/ASI/Personal%20Care/PC-12056_Oral_Care_Brochure.pdf).
International Search Report for International Application No. PCT/US2013/076885, provided by the International Search Authority, date mailed.
Sipomer® PAM-4000, Product Data Sheet n002195, Solvay Rhodia, 2012, Date Accessed: Aug. 23, 2016 (http://www.rhodia.com/product-literature-download.action?docId=0901663680d8e32e&docLanguage=EN&docType=TDS&output=BINARY&productName=Siporner+PAM-4000).
Schrader, 1989, "Grundlagen und Rezepturen der Kosmetica," Hilthig, Heidelberg pp. 628-631.

* cited by examiner

*Primary Examiner* — Brian Gulledge

(57) ABSTRACT

Provided is a mouth rinse composition comprising a phosphate/acrylate co-polymer and an orally acceptable carrier and methods of using the same.

18 Claims, No Drawings

ORAL CARE COMPOSITIONS AND METHODS

BACKGROUND

Many individuals desire a "bright" smile and white teeth, and consider dull and stained teeth cosmetically unattractive. Unfortunately, without preventive or remedial measures, stained teeth are almost inevitable due to the absorbent nature of dental material. Everyday activities such as smoking or other oral use of tobacco products, and eating, chewing or drinking certain foods and beverages (in particular coffee, tea and red wine), cause undesirable staining of surfaces of teeth. Staining can also result from microbial activity, including that associated with dental plaque. The chromogens or color causing substances in these materials become part of the pellicle layer and can permeate the enamel layer. Even with regular brushing and flossing, years of chromogen accumulation can impart noticeable tooth discoloration.

A tooth is comprised of an inner dentin layer and an outer hard enamel layer that is the protective layer of the tooth. The enamel layer of a tooth is naturally opaque, and white or a slightly off-white color. The enamel layer is composed of hydroxyapatite mineral crystals that create a somewhat porous surface. These hydroxyapatite crystals form microscopic hexagonal rods or prisms that make up the enamel surface. As a result, the surface of the enamel presents microscopic spaces or pores between the prisms. Without limiting the mechanism, function, or utility of the present disclosure, it is believed that this porous nature of the enamel is where discoloring substances permeate the enamel and discolor the teeth.

To combat staining and brighten or restore the natural enamel color, products containing bleaching materials are commercially available for professional and consumer use. The most commonly accepted chemicals used in teeth whitening today are peroxides. Peroxides are generally deemed safe from a physiological standpoint, and can be effective to whiten teeth. Such peroxides include hydrogen peroxide, carbamide peroxide, sodium perborate, and sodium percarbonate. When these peroxides are in appropriate contact with teeth they will usually oxidize stains, rendering the teeth whiter.

Professional dental treatments frequently include a tooth surface preparation such as acid etching followed by the application of highly concentrated bleaching solutions (e.g. up to 37% hydrogen peroxide) and/or the application of heat or light. (See, e.g., U.S. Pat. Nos. 5,425,953 and 5,766,574.) These procedures provide rapid results, but are expensive, and often require several trips to the dentist. In many cases, the patient's lips are uncomfortably retracted during the entire treatment and the patient is confined to sitting in the dental chair.

Alternatively, at home bleaching systems can be used. These systems have gained significant popularity in the past decade because of reduced cost, and increased convenience.

Current home treatment methods include abrasive toothpastes, toothpastes that produce oxides, whitening gels for use with a dental tray and whitening strips. The effectiveness of such techniques depends on a variety of factors including the type and intensity of the stain, the type of bleaching agent, contact time of the bleaching agent on the teeth, the amount of available bleaching active in the composition the ability of the bleaching agent to penetrate the tooth enamel, and consumer compliance. Effectiveness is also dependent on the amount of bleaching active in the composition, the ability of the active to be released during use, and the stability of the active in the product. However, the effectiveness of many of these treatments is adversely affected because of deficiencies in one or more factors relating to the composition and consumer compliance.

Biofilms form when bacteria adhere to surfaces in some form of watery environment and begin to excrete a slimy, glue-like substance that can stick to all kinds of materials—metals, plastics, soil particles, medical implant materials, biological tissues. Biofilms can be formed by a single bacterial species, but biofilms more often consist of many species of bacteria, as well as fungi, algae, protozoa, debris, and corrosion products. Essentially, a biofilm may form on any surface exposed to bacteria and some amount of water. Dental plaque is a yellowish biofilm that builds up on the teeth. Biofilms contain communities of disease-causing bacteria and their uncontrolled accumulation has been associated with cavities and gum disease (both gingivitis and periodontitis).

There is thus a need for novel oral compositions and methods that may inhibit staining, acid erosion, and/or biofilm formation.

BRIEF SUMMARY

Provided herein is a mouth rinse composition comprising a phosphate/acrylate co-polymer and an orally acceptable carrier.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

As used herein, an "oral care composition" refers to a composition for which the intended use can include oral care, oral hygiene, or oral appearance, or for which the intended method of use can comprise administration to the oral cavity. In some embodiments, an oral care composition is not intentionally swallowed, but is rather retained in the oral cavity for a time sufficient to affect the intended utility. The oral care compositions as disclosed herein may be used in nonhuman mammals such as companion animals (e.g., dogs and cats), as well as by humans. In some embodiments, the oral care compositions as disclosed herein are used by humans.

As used herein, "phosphate/acrylate co-polymer" refers to a polymer made up of acrylate monomers and phosphatebearing monomers, e.g., a co-polymerized product of a mixture of acrylic acid, methacrylic acid, and 2-hydroxyethyl methacrylate phosphates of Formula 1:

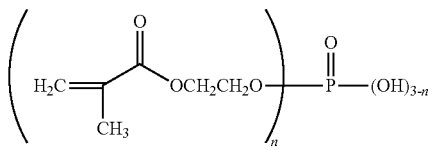

wherein n is 0, 1 or 2. In some embodiments, the phosphate/acrylate co-polymer is a co-polymerized product of a mixture of acrylic acid, methacrylic acid, and 2-hydroxyethyl methacrylate phosphates of Formula 1, comprising acrylic acid in a molar percentage of 70-90%, 80-90%, or about 85%; methacrylic acid in a molar percentage of 5-20%, 5-15%, or about 11%, and hydroxyethyl methacrylate phosphates of Formula 1 in a molar percentage of 1-10%, 2-6%, or about 4%. In some embodiments, the phosphate/acrylate co-polymer has a weight average molecular weight of from 10 to 500 kDa, optionally, 10 to 200 kDa, 10 to 40 kDa, 15 to 25, or 17 to 23 kDa, and the phosphate/acrylate co-polymer is below its glass transition temperature. In certain embodiments, the weight average molecular weight is 10 to 40 kDa. In other embodiments, the weight average molecular weight is 17 to 23 kDa. For example, in a particular embodiment, the phosphate/acrylate copolymer is a random copolymer that is the copolymerized product of a mixture of, in the relative amounts set forth in Table 1 below, 2-hydroxyethy methacrylate phosphates, acrylic acid, and methacrylic acid.

one carboxyl group. The acid contains an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrilacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other olefinic monomers copolymerizable with such carboxylic monomers include vinyl acetate, vinyl chloride, dimethyl maleate and the like. The synthetic anionic linear polycarboxylate is mainly a hydrocarbon with optional halogen and O-containing substituents and linkages as present in for example ester, ether, and OH groups. The copolymers preferably contain sufficient carboxylic salt groups for water-solubility. The terms "synthetic" and "linear" do not include known thickening or gelling agents comprising carboxymethylcellulose and other derivatives of cellulose and natural gums, nor Carbopols having reduced solubility due to cross-linkages.

In some embodiments, "synthetic anionic linear polycarboxylate" refers to 1:4 to 4:1 copolymers of maleic anhydride or acid with another polymerizable ethylenically unsaturated monomer, e.g., methyl vinyl ether (methoxyethylene), having a molecular weight (M.W.) of about 30,000 to about 2,500,000; for example 1:4 to 4:1, e.g. about 1:1, copolymers of methyl vinyl ether/maleic anhydride, wherein the anhydride is hydrolyzed following co-polymerization to provide the corresponding acid, having a molecular weight (M.W.) of about 30,000 to about 1,000,000, e.g. about

TABLE 1

| Monomer Name and Structure | Monomer Weight Ratio (weight %) | Monomer Molar Ratio (Mole %) |
|---|---|---|
| 2-hydroxyethyl methacylate phosphates<br><br>$\left( H_2C{=}\underset{CH_3}{C}{-}C({=}O){-}OCH_2CH_2O \right)_n \!\!-\!\! P({=}O){-}(OH)_{3-n}$<br><br>mixture of n = 0, n = 1, and n = 2 | 11 | 4 |
| acrylic acid<br><br>$H_2C{=}\underset{H}{C}{-}C({=}O){-}OH$ | 75 | 85 |
| methacrylic acid<br><br>$H_2C{=}\underset{CH_3}{C}{-}C({=}O){-}OH$ | 14 | 11 |

Phosphate/acrylate co-polymers as described include DV8801 (Rhodia).

As used herein. "synthetic anionic linear polycarboxylate" refers to a polymer synthesized by using an olefinically or ethylenically unsaturated carboxylic acid that contains an activated carbon-to-carbon olefinic double bond and at least 300,000 to about 800,000, e.g., as sold under the trade name GANTREZ®, e.g., GANTREZ® S-97 Pharmaceutical Grade (M.W. ca. 700,000), available from Ashland Specialty Chemicals, Bound Brook, N.J. 08805.

As used herein, "orally acceptable carrier" refers to any vehicle useful in formulating the oral care compositions disclosed herein. The orally acceptable carrier is not harmful to a mammal in amounts disclosed herein when retained in the mouth, without swallowing, for a period sufficient to permit effective contact with a dental surface as required herein. In general, the orally acceptable carrier is not harmful even if unintentionally swallowed. Suitable orally acceptable carriers can include, for example, one or more of the following: water, a buffer, a humectant, a surfactant, a sweetener, a flavorant, a pigment, a dye, an anti-caries agent, an anti-bacterial, a whitening agent, a desensitizing agent, a vitamin, a preservative, an enzyme, and mixtures thereof. In some preferred embodiments, the orally acceptable carrier is a mixture of one or more of water, a sugar alcohol such as sorbitol, glycerin and propylene glycol.

As used herein, a "tartar control agent" refers to a compound or a mixture of compounds that inhibit the formation of tartar, a mixture of calcium phosphates on organic matrices, and/or the deposition of plaque on teeth to form tartar (calculus).

As used herein, "chemical stain" refers to a discoloration of a dental surface caused by adsorption or absorption of a colored agent on or into the surface, or caused by chemical reaction of material of the dental surface (e.g., dental enamel) with a colored or noncolored agent contacting the surface. "Chemical staining" herein means formation and/or development of a chemical stain.

As used herein, "dental surface" refers to a surface of a natural tooth or a hard surface of artificial dentition including a denture, dental plate, crown, cap, filling, bridge, dental implant and the like. In some embodiments, the dental surface is a natural tooth.

The phosphate side group of a phosphate/acrylate co-polymer, as disclosed herein, may function as an anchor to deposit the co-polymer onto the tooth surface thereby forming a physical layer on the tooth surface that may inhibit staining and/or biofilm formation. The co-polymer may also prevent bacteria from sticking together.

Provided herein is a mouth rinse composition (Composition 1) comprising a phosphate/acrylate co-polymer, and an orally acceptable carrier.

Further provided herein is Composition 1 as follows:
1.1 Composition 1 wherein the composition comprises 0.1 to 10 weight % phosphate/acrylate co-polymer, e.g., 0.2 to 9 weight % phosphate/acrylate co-polymer, e.g., 0.3 to 8 weight % phosphate/acrylate co-polymer, e.g., 0.4 to 7 weight % phosphate/acrylate co-polymer, e.g., 0.5 to 6 phosphate/acrylate co-polymer, e.g., e.g., 0.5 to 5 weight % phosphate/acrylate co-polymer, e.g., 0.5 to 4 weight % phosphate/acrylate co-polymer, e.g., 0.5 to 3 weight % phosphate/acrylate co-polymer, e.g., 0.5 to 2 weight % phosphate/acrylate co-polymer, e.g., 1 to 10 weight % phosphate/acrylate co-polymer, e.g., 1 to 8 weight % phosphate/acrylate co-polymer, e.g., 1 to 6 weight % phosphate/acrylate co-polymer, e.g., 1 to 5 weight % phosphate/acrylate co-polymer, e.g., 1 to 4 weight % phosphate/acrylate co-polymer, e.g., 1 to 3 weight % phosphate/acrylate co-polymer, e.g., 1 to 2 weight % phosphate/acrylate co-polymer.
1.2 Composition 1 or 1.1 wherein the composition comprises 0.01 to 30 weight % synthetic anionic linear polycarboxylate, e.g., 0.1 to 30 weight % synthetic anionic linear polycarboxylate, e.g., 1 to 30 weight % synthetic anionic linear polycarboxylate, e.g., 5 to 30 weight % synthetic anionic linear polycarboxylate, e.g., 10 to 30 weight % synthetic anionic linear polycarboxylate, e.g., 10 to 20 weight % synthetic anionic linear polycarboxylate, e.g., 15 weight % synthetic anionic linear polycarboxylate, e.g., 17 weight % synthetic anionic linear polycarboxylate.
1.3 Composition 1, 1.1, or 1.2, wherein the synthetic anionic linear polycarboxylate is a copolymer of maleic anhydride and methyl vinyl ether.
1.4 Composition 1 or 1.1-1.3 wherein the synthetic anionic linear polycarboxylate is a 1:4 to 4:1 copolymer of methyl vinyl ether/maleic anhydride (optionally fully or partially hydrolyzed following co-polymerization to provide the corresponding acid)
1.5 Composition 1 or 1.1-1.4 wherein the synthetic anionic linear polycarboxylate has a molecular weight (M.W.) of about 30,000 to about 1,000,000. e.g. about 300,000 to about 800,000.
1.6 Any foregoing composition wherein the phosphate/acrylate co-polymer is a co-polymerized product of a mixture of acrylic acid, methacrylic acid, and 2-hydroxyethyl methacrylate phosphates of Formula 1:

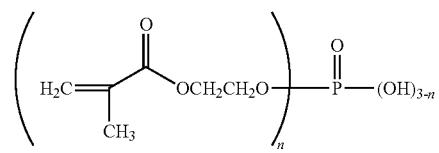

wherein n is 0, 1 or 2.
1.7 Any foregoing composition wherein the phosphate/acrylate co-polymer is a co-polymerized product of a mixture of acrylic acid, methacrylic acid, and 2-hydroxyethyl methacrylate phosphates of Formula 1 comprising acrylic acid in a molar percentage of 80-90%, e.g., about 85%; methacrylic acid in a molar percentage of 5-15%, e.g., about 11%, and hydroxyethyl methacrylate phosphates of Formula 1 in a molar percentage of 2-6%, e.g., about 4%.
1.8 Any foregoing composition wherein the phosphate/acrylate co-polymer has an average molecular weight of from 10 to 40 kDa, e.g., 20 to 30 kDa; or from 30 to 50 kDa, e.g., 40 kDa; or from 90 to 110 kDa, e.g. 98 kDa; or from 100 to 120 kDa, e.g., 109 kDa; or from 120 to 140 kDa, e.g. 131 kDa; or from 185 to 205 kDa, e.g., 195 kDa.
1.9 Any foregoing composition wherein the phosphate/acrylate copolymer is a random copolymer having a weight average molecular weight of about 20,000 to 30,000 grams per mole or 35,000 to 45,000 grams per mole that is the copolymerized product of a mixture of acrylic acid, methacrylic acid, and 2-hydroxyethy methacrylate phosphates of Formula 1, e.g., in a molar ratio of about 85:11:4.
1.10 Any foregoing composition wherein the composition comprises an anti-bacterial.
1.11 Composition 1.10 wherein the anti-bacterial agent is triclosan, cetylpyridinium chloride (CPC), chlorhexidine (CHX), stannous salts, essential oils, water soluble zinc salts, water insoluble zinc salts, e.g., ZnO or zinc citrate, or a mixture thereof, e.g., wherein the anti-bacterial agent is triclosan, e.g., wherein the anti-bacterial agent is ZnO. e.g., wherein the anti-bacterial agent is zinc citrate, e.g., wherein the anti-bacterial agent is a mixture thereof.
1.12 Composition 1.10 wherein the anti-bacterial agent is a zinc salt, or a mono-, di- or trihydrate of a zinc salt.
1.13 Composition 1.10 wherein the anti-bacterial agent is zinc citrate trihydrate.

1.14 Any foregoing composition wherein the composition comprises a pyrophosphate salt.

1.15 Any foregoing composition wherein the composition comprises a pyrophosphate salt selected from the group consisting of tetrasodium pyrophosphate and tetrapotassium pyrophosphate.

1.16 Any foregoing composition wherein the composition comprises water.

1.17 Any foregoing composition wherein the composition comprises a mixture of glycerin, sorbitol, and propylene glycol; for example glycerin in an amount of from 5% to 10%, for example 7.5%; for example sorbitol in an amount of from 3% to 8% sorbitol (70%), for example 5.5%; and for example propylene glycol in an amount of from 5% to 10%, for example 7%.

1.18 Any foregoing composition wherein the composition comprises a sweetener.

1.19 Composition 1.16 wherein the sweetener is sodium saccharin.

1.20 Any foregoing composition wherein the composition comprises a flavorant.

1.21 Any foregoing composition wherein the composition comprises a pigment.

1.22 Any foregoing composition wherein the composition comprises:
  phosphate/acrylate co-polymer in an amount of from 0.4% to 2.4%;
  synthetic anionic linear polycarboxylates in an amount of from 0.01% to 2%;
  a zinc salt in an amount of from 0.01% to 2%; and
  one or more pyrophosphate salts in an aggregate amount of from 0.1% to 3%.

1.23 Composition 1.22, wherein:
  the phosphate/acrylate co-polymer is DV8801;
  the synthetic anionic linear polycarboxylates is GANTREZ® S-97;
  the zinc salt is zinc citrate, or a hydrate thereof; and
  the pyrophosphate salts are sodium pyrophosphate and potassium pyrophosphate.

1.24 Any foregoing composition wherein the composition comprises a desensitizing agent, a vitamin, a preservative, an enzyme, or a mixture thereof.

In some embodiments, the oral care compositions disclosed herein, e.g., Composition 1, e.g., 1.1-1.24, comprise water. Water employed in the preparation of the oral care compositions disclosed herein, e.g., Composition 1, e.g., 1.1-1.24, should be deionized and free of organic impurities. Water may make up the balance of the oral care composition. In some embodiments, the oral care compositions disclosed herein, e.g., Composition 1, e.g., 1.1-1.24, comprise 0 to 90 weight % water, e.g., 0.1 to 90 weight % water, e.g., 1 to 80 weight % water, e.g., 2 to 70 weight % water, 5 to 60 weight % water, e.g., 5 to 50 weight % water, e.g., 20 to 60 weight % water, e.g., 10 to 40 weight % water. This amount of water includes the free water which is added plus that amount which is introduced with other components of the oral care composition, such as with sorbitol.

A buffer can optionally be used to adjust the pH of oral care compositions, for example, to a range of about pH 4.0 to about pH 7.0. In some embodiments, the oral care compositions disclosed herein, e.g., Composition 1, e.g., 1.1-1.24, comprise from 0.1 to 10 weight % of a buffer, 0.5 to 10 weight % of a buffer, e.g., 0.5 to 5 weight % of a buffer. e.g., 0.5 to 4 weight % of a buffer, e.g., 0.5 to 3 weight % of a buffer, e.g., 0.5 to 2 weight % of a buffer, e.g., 1 to 2 weight % of a buffer. Buffers that may be used in the oral care compositions disclosed herein, e.g., Composition 1, e.g., 1.1-1.40, include, for example, sodium bicarbonate, sodium phosphate {e.g., monosodium phosphate (NaH$_2$PO$_4$), disodium phosphate (Na$_2$HPO$_4$), trisodium phosphate (Na$_3$PO$_4$)}, sodium hydroxide, sodium carbonate, sodium acid pyrophosphate, citric acid, sodium citrate, and mixtures thereof. In some embodiments, sodium hydroxide is used as the buffer in the oral care compositions disclosed herein, e.g., Composition 1, e.g., 1.1-1.24. In some embodiments, the oral care compositions disclosed herein, e.g., Composition 1, e.g., 1.1-1.24, comprise from 0.1 to 10 weight % of sodium hydroxide, e.g., 0.5 to 10 weight % of sodium hydroxide. e.g., 0.5 to 5 weight % of sodium hydroxide, e.g., 0.5 to 4 weight % of sodium hydroxide, e.g., 0.5 to 3 weight % of sodium hydroxide, e.g., 0.5 to 2 weight % of sodium hydroxide, e.g., 1 to 2 weight % of sodium hydroxide.

One or more humectants keep the oral cavity moist after application of the mouthwash. Certain humectants can also impart desirable sweetness or flavor to oral care compositions. In some embodiments, the oral care compositions disclosed herein, e.g., Composition 1, e.g., 1.1-1.24, comprise, on a pure humectant basis, from 0 to 70 weight % of a humectant, e.g., 10 to 70 weight % of a humectant, e.g., 10 to 65 weight % of a humectant, e.g., 10 to 60 weight % of a humectant, e.g., 10 to 50 weight % of a humectant, e.g., 10 to 30 weight % of a humectant, e.g., 20 to 50 weight % of at a humectant, e.g., 20 to 40 weight % of a humectant. Humectants that may be used in the oral care compositions disclosed herein, e.g., Composition 1, e.g., 1.1-1.24, include, for example, one or more of glycerin, sorbitol, xylitol, butylene glycol, polyethylene glycol, propylene glycol, trimethyl glycine, and mixtures thereof. In some embodiments, a mixture of glycerin, sorbitol, and propylene glycol is used as the humectant in the oral care compositions disclosed herein, e.g., Composition 1, e.g., 1.1-1.24. In some embodiments, the oral care compositions disclosed herein, e.g., Composition 1, e.g., 1.1-1.24, comprise, on a pure humectant basis, from 0 to 70 weight % of glycerin, sorbitol, and propylene glycol, e.g., 10 to 70 weight % of glycerin, sorbitol, and propylene glycol, e.g., 10 to 65 weight % of glycerin, sorbitol, and propylene glycol, e.g., 10 to 60 weight % of glycerin, sorbitol, and propylene glycol, e.g., 10 to 50 weight % of glycerin, sorbitol, and propylene glycol, e.g., 10 to 30 weight % of glycerin, sorbitol, and propylene glycol, e.g., 20 to 50 weight % of glycerin, sorbitol, and propylene glycol, e.g., 20 to 40 weight % of glycerin, sorbitol, and propylene glycol.

In some embodiments, the oral care compositions disclosed herein, e.g., Composition 1, e.g., 1.1-1.24, comprise a detergent or surfactant, e.g., selected from anionic, cationic, zwitterionic, and nonionic surfactants, and mixtures thereof. In some embodiments, the surfactant is reasonably stable throughout a wide pH range. Surfactants are described in, for example, U.S. Pat. No. 3,959,458, to Agricola et al; U.S. Pat. No. 3,937,807, to Haefele; and U.S. Pat. No. 4,051,234, to Gieske et al. In some embodiments, the oral care compositions disclosed herein, e.g., Composition 1. e.g., 1.1-1.24, comprise from 0.01 to 10 weight % of a surfactant, e.g., 0.05 to 5 weight % of a surfactant, e.g., 0.1 to 10 weight % of a surfactant, e.g., 0.1 to 5 weight % of a surfactant, e.g., 0.1 to 2 weight % of a surfactant, e.g., 0.5 to 2 weight % of a surfactant. In some embodiments, the oral care compositions disclosed herein, e.g., Composition 1, e.g., 1.1-1.24, comprise from 0.01 to 10 weight % of an nonionic surfactant, e.g., 0.05 to 5 weight % of nonionic surfactant, e.g., 0.1 to 10 weight % of an nonionic surfactant, e.g., 0.1 to 5 weight % of an nonionic surfactant, e.g., 0.1 to 2 weight % of an nonionic surfactant, e.g., 0.5 to 2 weight % of an nonionic surfactant, e.g., 1 weight % of an nonionic surfactant. In some embodiments, the surfactant, for example nonionic surfactant, can also function as an emulsifier. One preferred example of such a surfactant is polysorbate 20.

In some embodiments, the oral care compositions disclosed herein, e.g., Composition 1, e.g., 1.1-1.40, comprise a sweetener. In some embodiments, the oral care compositions disclosed herein, e.g., Composition 1, e.g., 1.1-1.24, comprise 0.005 to 10 weight % of a sweetener, e.g., 0.01 to 10 weight % of a sweetener, e.g., 0.1 to 10 weight % of a sweetener, e.g., from 0.1 to 5 weight % of a sweetener, e.g., from 0.1 to 3 weight % of a sweetener, e.g., from 0.1 to 1 weight % of a sweetener. e.g., from 0.1 to 0.5 weight % of a sweetener. Sweeteners that may be used in the oral care compositions disclosed herein, e.g., Composition 1. e.g., 1.1-1.24, include, for example, sucrose, glucose, saccharin, sucralose, dextrose, levulose, lactose, mannitol, sorbitol, fructose, maltose, xylitol, saccharin salts (e.g., sodium saccharin), thaumatin, aspartame, D-tryptophan, dihydrochalcones, acesulfame, cyclamate salts, and mixtures thereof. In some embodiments, sodium saccharin is used as the sweetener in the oral care compositions disclosed herein, e.g., Composition 1, e.g., 1.1-1.24. In some embodiments, the oral care compositions disclosed herein, e.g., Composition 1. e.g., 1.1-1.24, comprise 0.005 to 10 weight % sodium saccharin, e.g., 0.01 to 1 weight % sodium saccharin, e.g., 0.01 to 0.5 weight % sodium saccharin, e.g., from 0.01 to 0.03 weight % sodium saccharin, e.g., 0.02 weight % sodium saccharin.

In some embodiments, the oral care compositions disclosed herein, e.g., Composition 1, e.g., 1.1-1.24, comprise a flavorant. In some embodiments, the oral care compositions disclosed herein, e.g., Composition 1, e.g., 1.1-1.24, comprise 0.01 to 5 weight % of a flavorant, e.g., 0.01 to 4 weight % of a flavorant, e.g., 0.01 to 3 weight % of a flavorant, e.g., 0.01 to 2 weight % of a flavorant, e.g., 0.05 to 0.5 weight % of a flavorant, e.g., 0.05 to 0.15 weight % of a flavorant, e.g., 0.05 to 2 weight % of a flavorant, e.g., 0.5 to 2 weight % of a flavorant, e.g., 0.7 to 2 weight % of a flavorant, e.g., 0.8 to 2 weight % of a flavorant e.g., 0.9 to 2 weight % of a flavorant, e.g., 1 to 2 weight % of a flavorant. Flavorants that may be used in the oral care compositions disclosed herein, e.g., Composition 1, e.g., 1.1-1.24, include, for example, essential oils, as well as various flavoring aldehydes, esters, alcohols, and similar materials, as well as menthol, carvone, and anethole, as well as mixtures thereof. Examples of essential oils include oils of spearmint, peppermint, wintergreen, sassafras, clove, sage, eucalyptus, marjoram, cinnamon, lemon, lime, grapefruit, and orange. In some embodiments, a mixture of wintergreen (methyl salicylate) and menthol, e.g., menthol levo, is used as the flavorant in the oral care compositions disclosed herein, e.g., Composition 1, e.g., 1.1-1.24, for example in an amount of from 0.01 to 0.2 weight percent each. It will be appreciated that methyl salicylate can also function as an antiseptic in the oral care compositions disclosed herein, e.g., Composition 1, e.g., 1.1-1.24.

In some embodiments, the oral care compositions disclosed herein, e.g., Composition 1, e.g., 1.1-1.40, further comprise an anti-caries agent. In some embodiments, the oral care compositions disclosed herein, e.g., Composition 1. e.g., 1.1-1.40, comprise 0.005 to 10 weight % of the anti-caries agent, e.g., 0.01 to 10 weight % of the anti-caries agent, e.g., 0.01 to 5 weight % of the anti-caries agent, e.g., 0.01 to 1 weight % of the anti-caries agent, e.g., 0.01 to 0.3 weight % of the anti-caries agent, e.g., 0.1 to 10 weight % of the anti-caries agent, e.g., 0.1 to 5 weight % of the anti-caries agent, e.g., 0.1 to 2 weight % of the anti-caries agent, e.g., 0.1 to 1 weight % of the anti-caries agent, e.g., 0.1 to 0.8 weight % of the anti-caries agent, e.g., 0.1 to 0.6 weight % of the anti-caries agent, e.g., 0.1 to 0.5 weight % of the anti-caries agent. In some embodiments, the anti-caries agent is a fluoride ion source. In some embodiments, the oral care compositions disclosed herein, e.g., Composition 1. e.g., 1.1-1.40, further comprise 0.005 to 10 weight % of the anti-caries agent which is a fluoride ion source, e.g., 0.01 to 10 weight % of the anti-caries agent which is a fluoride ion source, e.g., 0.01 to 5 weight % of the anti-caries agent which is a fluoride ion source, e.g., 0.01 to 1 weight % of the anti-caries agent which is a fluoride ion source, e.g., 0.01 to 0.3 weight % of the anti-caries agent which is a fluoride ion source, e.g., 0.1 to 10 weight % of the anti-caries agent which is a fluoride ion source, e.g., 0.1 to 5 weight % of the anti-caries agent which is a fluoride ion source, e.g., 0.1 to 2 weight % of the anti-caries agent which is a fluoride ion source, e.g., 0.1 to 1 weight % of the anti-caries agent which is a fluoride ion source, e.g., 0.1 to 0.8 weight % of the anti-caries agent which is a fluoride ion source, e.g., 0.1 to 0.6 weight % of the anti-caries agent which is a fluoride ion source, e.g., 0.1 to 0.5 weight % of the anti-caries agent which is a fluoride ion source. Examples of fluoride ion sources that may be used in the oral compositions disclosed herein, e.g., Composition 1, e.g., 1.1-1.40, are found in U.S. Pat. No. 3,535,421 to Briner et al.; U.S. Pat. No. 4,885,155 to Parran, Jr. et al., and U.S. Pat. No. 3,678,154 to Widder et al. Other examples of fluoride ion sources include, for example, stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof. In certain embodiments the fluoride ion source includes stannous fluoride, sodium fluoride, and sodium monofluorophosphate, as well as mixtures thereof. In some embodiments, the anti-caries agent is sodium fluoride. In some embodiments, the oral care compositions disclosed herein, e.g., Composition 1, e.g., 1.1-1.40, comprise 0.005 to 10 weight % sodium fluoride, e.g., 0.01 to 10 weight % sodium fluoride, e.g., 0.01 to 5 weight % sodium fluoride, e.g., 0.01 to 1 weight % sodium fluoride, e.g., 0.01 to 0.3 weight % sodium fluoride, e.g., 0.1 to 10 weight % sodium fluoride, e.g., 0.1 to 5 weight % sodium fluoride, e.g., 0.1 to 2 weight % sodium fluoride, e.g., 0.1 to 1 weight % sodium fluoride, e.g., 0.1 to 0.8 weight % sodium fluoride, e.g., 0.1 to 0.6 weight % sodium fluoride, e.g., 0.1 to 0.5 weight % sodium fluoride.

In some embodiments, the oral care compositions disclosed herein, e.g., Composition 1, e.g., 1.1-1.40, comprise the anti-caries agent which is a fluoride ion source in an amount sufficient to supply 25 ppm to 25,000 ppm of fluoride ions, e.g., from 100 to 20,000 ppm of fluoride ions, e.g., from 300 to 15,000 ppm of fluoride ions, e.g., from 500 to 10,000 ppm of fluoride ions. e.g., from 500 to 8.000 ppm of fluoride ions, e.g., from 500 to 6,000 ppm of fluoride ions, e.g., from 500 to 4.000 ppm of fluoride ions, e.g., from 500 to 2,000 ppm of fluoride ions. e.g., from 500 to 1,800 ppm of fluoride ions, e.g., from 1000 to 1600 ppm. e.g., 1450 ppm of fluoride ions. The appropriate level of fluoride ions will depend on the particular application. In some embodiments, a toothpaste for consumer use comprises the anti-caries agent which is a fluoride ion source in an amount sufficient to supply from 1.000 to 1,500 ppm of fluoride ions, with pediatric toothpaste having somewhat less. In some embodiments, a dentifrice or coating for professional application comprises the anti-caries agent which is a fluoride ion source in an amount sufficient to supply from 5,000 to 25,000 ppm of fluoride ions.

In some embodiments, the oral care compositions disclosed herein, e.g., Composition 1, e.g., 1.1-1.24, comprise an anti-bacterial. In some embodiments, the oral care compositions disclosed herein, e.g., Composition 1, e.g., 1.1-1.24, comprise 0.01 to 10 weight % of an anti-bacterial, e.g., 0.1 to 10 weight % of an anti-bacterial. e.g., 0.5 to 5 weight % of an anti-bacterial, e.g., 0.01 to 5 weight % of an anti-bacterial, e.g., 0.05 to 4 weight % of an anti-bacterial, e.g., 0.05 to 3 weight % of an anti-bacterial, e.g., 0.05 to 2 weight % of an anti-bacterial, e.g., 0.05 to 1 weight % of an anti-bacterial, e.g., 0.1 to 1 weight % of an anti-bacterial, e.g., 0.1 to 0.5 weight % of an anti-bacterial. The amount of the anti-bacterial will vary depending on the type of oral care composition. Examples of anti-bacterials that may be used in the oral compositions disclosed herein, e.g., Composition 1, e.g., 1.1-1.24, include, for example, halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC). N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts, and mixtures thereof. In some embodiments, the anti-bacterial is a zinc salt, for example zinc citrate. In some embodiments, the oral care compositions disclosed herein, e.g., Composition 1. e.g., 1.1-1.24, comprise 0.01 to 10 weight % zinc citrate, e.g., 0.1 to 10 weight % zinc citrate, e.g., 0.5 to 5 weight % zinc citrate, e.g., 0.01 to 5 weight % zinc citrate, e.g., 0.05 to 4 weight % zinc citrate, e.g., 0.05 to 3 weight % zinc citrate, e.g., 0.05 to 2 weight % zinc citrate. e.g., 0.05 to 1 weight % zinc citrate, e.g., 0.1 to 1 weight % zinc citrate, e.g., 0.1 to 0.5 weight % zinc citrate.

In some embodiments, an oral care composition disclosed herein comprises:

| Ingredient | % |
| --- | --- |
| 70% Sorbitol | 5.5 |
| 99.0%-101.0% Glycerin | 7.5 |
| Water | Q.S. |
| Propylene Glycol | 7 |
| Gantrez S-97 (B.F.) - Liquid (13% assay) | 0.25 |
| Zinc Citrate Trihydrate | 0.28 |
| Phosphate/acrylate polymer | 0.400-2.400 |
| Tetrapotassium Pyrophosphate | 1.35 |
| Polysorbate 20 | 1 |
| Sodium Benzoate | 0.5 |
| Tetrasodium Pyrophosphate | 0.45 |
| Menthol Levo | 0.1 |
| Methyl Salicylate | 0.1 |
| Sodium Saccharin | 0.02 |

Further provided is a method (Method A) for the treatment and/or inhibition of a chemical stain, plaque, and/or tartar on a dental surface, comprising contacting the dental surface with any of the preceding oral care compositions.

Further provided herein is Method A as follows:

A.1 Method A wherein the composition is Composition 1, e.g., 1.1-1.24.

A.2 Method A or A.1 wherein the method is for the treatment of a chemical stain, plaque, acid erosion, and/or tartar on the dental surface.

A.3 Method A.2 wherein the method is for the treatment of a chemical stain on the dental surface.

A.4 Method A.2 wherein the method is for the treatment of plaque on the dental surface.

A.5 Method A.2 wherein the method is for the treatment of acid erosion on the dental surface.

A.6 Method A.2 wherein the method is for the treatment of tartar on the dental surface.

A.7 Method A or A.1 wherein the method is for the inhibition of a chemical stain, plaque, and/or tartar on the dental surface.

A.8 Method A.7 wherein the method is for the inhibition of a chemical stain on the dental surface.

A.9 Method A.7 wherein the method is for the inhibition of plaque on the dental surface.

A.10 Method A.7 wherein the method is for the inhibition of acid erosion on the dental surface.

A.11 Method A.7 wherein the method is for the inhibition of tartar on the dental surface.

A.12 Method A or A.1-A.11 wherein the dental surface is a human tooth.

A.13 Method A or A.1-A.12 wherein the composition is contacted with the dental surface by brushing.

Further provided is a method (Method B) for the treatment and/or inhibition of gum disease comprising contacting the oral cavity with any of the preceding oral care compositions.

Further provided herein is Method B as follows:

B.1 Method B wherein the composition is Composition 1, e.g., 1.1-1.24.

B.2 Method B or B.1 wherein the method is for the treatment of gum disease.

B.3 Method B, B.1, or B.2 wherein the gum disease is gingivitis.

B.4 Method B, B.1, or B wherein the gum disease is periodontitis.

B.5 Method B or B.1 wherein the method is for the inhibition of gum disease.

B.6 Method B, B.1, or B.5 wherein the gum disease is gingivitis.

B.7 Method B, B.1, or B.5 wherein the gum disease is periodontitis.

B.8 Method B or B.1-B.7 wherein the oral cavity is a human oral cavity.

B.9 Method B or B.1-B.8 wherein the composition is contacted with the oral cavity by rinsing.

Further provided is a method (Method C) for the treatment and/or inhibition of halitosis comprising contacting the oral cavity with any of the preceding oral care compositions.

Further provided herein is Method C as follows:

C.1 Method C wherein the composition is Composition 1, e.g., 1.1-1.24.

C.2 Method C or C.1 wherein the oral cavity is a human oral cavity.

C.3 Method C, C.1, or C.2 wherein the composition is contacted with the oral cavity by rinsing.

Further provided is a method (Method D) for inhibiting biofilm formation on a dental surface comprising contacting the dental surface with any of the preceding oral care compositions.

Further provided herein is Method D as follows:

D.1 Method D wherein the composition is Composition 1, e.g., 1.1-1.24.

D.2 Method D or D.1 wherein the dental surface is a human tooth.

D.3 Method D, D.1, or D.2 wherein the composition is contacted with the dental surface by rinsing.

Further provided is a use (Use A) of any of the preceding oral care compositions for the treatment and/or inhibition of a chemical stain, plaque, and/or tartar on a dental surface comprising contacting the dental surface with any of the preceding oral care compositions.

Further provided herein is Use A as follows:

A.1 Use A wherein the composition is Composition 1, e.g., 1.1-1.24.

A.2 Use A or A.1 wherein the use is for the treatment of a chemical stain, plaque, acid erosion, and/or tartar on the dental surface.

A.3 Use A.2 wherein the use is for the treatment of a chemical stain on the dental surface.

A.4 Use A.2 wherein the use is for the treatment of plaque on the dental surface.

A.5 Use A2 wherein the use is for the treatment of acid erosion on the dental surface.

A.6 Use A.2 wherein the use is for the treatment of tartar on the dental surface.

A.7 Use A or A.1 wherein the use is for the inhibition of a chemical stain, plaque, acid erosion, and/or tartar on the dental surface.

A.8 Use A.7 wherein the use is for the inhibition of a chemical stain on the dental surface.

A.9 Use A.7 wherein the use is for the inhibition of plaque on the dental surface.

A.10 Use A.7 wherein the use is for the inhibition of acid erosion on the dental surface.

A.11 Use A.7 wherein the use is for the inhibition of tartar on the dental surface.

A.12 Use A or A.1-A.11 wherein the dental surface is a human tooth.

A.13 Use A or A.1-A.12 wherein the composition is contacted with the dental surface by brushing.

Further provided is a use (Use B) of any of the preceding oral care compositions for the treatment and/or inhibition of gum disease in an oral cavity comprising contacting the oral cavity with any of the preceding oral care compositions.

Further provided herein is Use B as follows:

B.1 Use B wherein the composition is Composition 1, e.g., 1.1-1.57.

B.2 Use B or B.1 wherein the use is for the treatment of gum disease.

B.3 Use B, B.1, or B.2 wherein the gum disease is gingivitis.

B.4 Use B, B.1, or B wherein the gum disease is periodontitis.

B.5 Use B or B.1 wherein the use is for the inhibition of gum disease.

B.6 Use B, B.1, or B.5 wherein the gum disease is gingivitis.

B.7 Use B, B.1, or B.5 wherein the gum disease is periodontitis.

B.8 Use B or B.1-B.7 wherein the oral cavity is a human oral cavity.

B.9 Use B or B.1-B.8 wherein the composition is contacted with the oral cavity by rinsing.

Further provided is a use (Use C) of any of the preceding oral care compositions for the treatment and/or inhibition of halitosis in an oral cavity comprising contacting the oral cavity with any of the preceding oral care compositions.

Further provided herein is Use C as follows:

C.1 Use C wherein the composition is Composition 1, e.g., 1.1-1.57.

C.2 Use C or C.1 wherein the oral cavity is a human oral cavity.

C.3 Use C, C.1, or C.2 wherein the composition is contacted with the oral cavity by rinsing.

Further provided is a use (Use D) of any of the preceding oral care compositions for the inhibition of biofilm formation on a dental surface comprising contacting the dental surface with any of the preceding oral care compositions.

Further provided herein is Use D as follows:

D.1 Use D wherein the composition is Composition 1, e.g., 1.1-1.57.

D.2 Use D or D.1 wherein the oral cavity is a human oral cavity.

D.3 Use D, D.1, or D.2 wherein the composition is contacted with the oral cavity by rinsing.

As used herein, "inhibition" refers to reduction of stains that would otherwise form or develop subsequent to the time of the treatment. Such inhibition can range from a small but observable or measurable reduction to complete inhibition of subsequent staining, by comparison with an untreated or placebo-treated dental surface.

Where the dental surface is substantially free of chemical stains, Method A, e.g., A.1-A.10, and Use B, e.g., B.1-B.10, are effective to inhibit formation and development of new chemical stains, as can occur for example by oral use of tobacco products (including smoking) or by drinking tea or coffee, subsequent to treatment according to the method. Where the dental surface already possesses some degree of chemical staining. Method A, e.g., A.1-A.10, and Use B, e.g., B.1-B.10, are effective to inhibit further development of the existing stain. In some embodiments, the Method A, e.g., A.1-A.10, and Use B, e.g., B.1-B.10, can remove, partially or completely, an existing chemical stain as well as inhibit subsequent staining.

EXAMPLES

Example 1

Mouth Rinse Composition

Without being bound by theory, it is believed that GANTREZ® polymers, and in particular GANTREZ® S-97 may help phosphate/acrylate co-polymer deposit on a dental surface due to its film forming property even though the phosphate group as the side group in the phosphate/acrylate co-polymer can anchor itself as well. Accordingly, a Mouth Rinse was formulated containing a phosphate/acrylate co-polymer and a GANTREZ® S-97/Pyrophosphate/Zinc system, as shown in Table 2 below.

TABLE 2

Mouth Rinse Formulation

| Ingredient | % |
|---|---|
| 70% Sorbitol | 5.5 |
| 99.0%-101.0% Glycerin | 7.5 |
| Water | Q.S. |
| Propylene Glycol | 7 |
| Gantrez S-97 (B.F.) - Liquid (13% assay) | 0.25 |
| Zinc Citrate Trihydrate | 0.28 |
| Phosphate/acrylate co-polymer (as a.i.) | 0.4-2.4 |
| Tetrapotassium Pyrophosphate | 1.35 |
| Polysorbate 20 | 1 |
| Sodium Benzoate | 0.5 |
| Tetrasodium Pyrophosphate | 0.45 |
| Menthol Levo | 0.1 |
| Methyl Salicylate | 0.1 |
| Sodium Saccharin | 0.02 |

Example 2

In Vitro Stain Inhibition Test

The in vitro stain inhibition test is conducted on hydroxyapatite disc (HAP disc) and the efficacy is quantified by measuring the light reflected from the surface of HAP disc after treatment with the mouth rinse and subsequent exposure to a staining agent, in this case, coffee. The measurement is taken with a chromameter and L*a*b* value recorded. The HAP disc is first soaked in saliva overnight and baseline whiteness is measured, next it is treated with the mouth rinse of Example 1 for 5 minutes and the initial L*a*b* is recorded right away. After that, the HAP disc is exposed to a coffee stain for 15 minutes, rinsed with distilled ionized water and incubated in saliva for 20 minutes. The above staining process is repeated a total three times and the final L*a*b* is read again which would compare to initial L*a*b* to show how well the dentifrice could prevent the coffee stain from forming on the HAP disc. The less the delta L*, the better stain prevention effect provided by the dentifrice. The test results showed that the water control produced a ΔL of 37.24; the formulation of Example 1 without phosphate/acrylate co-polymer provided a ΔL of 21.39, and the formulation of Example 1 with 0.4% phosphate/acrylate co-polymer provided a ΔL of 16.59, indicating that the phosphate/acrylate polymer enhances stain prevention efficacy beyond that of the Gantrez/pyrophosphate/zinc system.

Example 3

Anti-Erosion Efficacy

The anti-erosion efficacy of the phosphate/acrylate co-polymer was determined by the following procedure:

pH Stat: Each polymer stock was diluted to 1% w/v in DI water. Sintered hydroxyapatite disks (2ea) were immersed in 0.3% citric acid pH 3.8 for 15 minutes and the dissolution rate measured using a Metrohm pH stat (untreated control rate) with thermostat set to 37° C. The average dissolution rate from 3 consecutive control runs was determined. The disks were then treated with 10 mL of the test polymer 1% solution for minutes, rinsed with 10 ml DI water and the dissolution rate measured again with the pH stat again for 15 minutes (Challenge 1) and a subsequent 15 minutes (Challenge 2). % Reduction in HAP dissolution rate was determined as [1−(challenge rate/untreated control rate)]*100%. A higher % reduction indicates a better ability of the polymer to protect the HAP from acid dissolution/erosion. Each polymer was tested in duplicate. Chitosan polymer (Primex CG800) and fluoride rinse were included as positive controls.

Calcium Analysis: Sintered HAP disks were treated for 2 minutes with 2 ml of the 1% polymer solution or phosphate buffer control, rinsed with PBS and then challenged for 5 minutes with 2 ml of 1% citric acid pH 3.8. The disks were removed and the citric acid calcium concentration were determined by atomic absorption. A lower calcium concentration represents better protection. The results are shown in Table 3 below.

TABLE 3

Results of Anti-Erosion Efficacy Test

| Sample | Polymer MW | P Content (relative to Phosphate/ acrylate co-polymer 1) | % Reduction Challenge 1 | % Reduction Challenge 2 | Ppm Calcium from Calcium Analysis* |
|---|---|---|---|---|---|
| Phosphate/acrylate co-polymer 1 (DV8801) | 40,000 | 1 | 8 | 14 | 32 |
| DV9394 | 98,000 | 1.56 | 9 | 9 | nd |
| DV9393 | 109,000 | 1.25 | 10 | 11 | nd |
| Phosphate/acrylate co-polymer 2 (DV8801) | 131,000 | 1 | 20 | 22 | 21 |
| DV9394 | 195,000 | 1.56 | 12 | 13 | 27 |
| Commercially available chitosan 0.15% | 330,000 | N/A | 37 | 27 | Nd |
| Commercial fluoride rinse 225 ppm F | N/A | N/A | 21 | 5 | Nd |

*For comparison, phosphate buffer control sample was 29 ppm calcium
nd = not determined All the phosphate/acrylate co-polymers provided reduction in HAP dissolution at 1% w/v with the higher molecular weight phosphate/acrylate co-polymer providing the most significant protection. Notably, the protection was resistant to multiple challenges, unlike the commercially available controls.

Example 4

Dose Response Studies

The phosphate/acrylate co-polymers were evaluated at 1% and 10% using the pH stat model described above, except with pH 2.8 0.3% citric acid used as the challenge solution, representing a stronger acid challenge. The Results are shown in Table 4 below.

TABLE 4

Results of Dose Response Study

| Polymer | 1% Polymer % Reduction | 10% Polymer % Reduction |
|---|---|---|
| phosphate/acrylate co-polymer MW 40,000 (DV8801) | 9 | 28 |
| phosphate/acrylate co-polymer MW 131,000 (DV8801) | 25 | 32 |

The dose response studies indicate that molecular weight is important, with the lower molecular weight polymer requiring a higher dosage to achieve similar results to the higher molecular weight variants. In addition, the results confirm that protection extends down to pH 2.8, which is representative of soft drink challenge.

What is claimed is:

1. A mouth rinse composition comprising a phosphate/acrylate co-polymer and an orally acceptable carrier, wherein the phosphate/acrylate co-polymer is a co-polymerized product of a mixture of acrylic acid, methacrylic acid, and a mixture of 2-hydroxyethyl methacrylate phosphates of Formula 1:

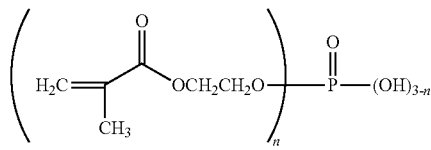

wherein n is 0, 1 or 2.

2. The composition of claim 1, wherein the composition comprises 0.1 weight % to 10 weight % of the phosphate/acrylate co-polymer.

3. The composition of claim 1, wherein the composition comprises 0.01 to 30 weight % synthetic anionic linear polycarboxylate.

4. The composition of claim 3, wherein the synthetic anionic linear polycarboxylate is a copolymer of maleic anhydride or acid and methyl vinyl ether.

5. The composition of claim 4, wherein the synthetic anionic linear polycarboxylate is 1:4 to 4:1 copolymer of methyl vinyl ether and maleic anhydride, wherein the anhydride is hydrolyzed after co-polymerization to provide the acid, having a molecular weight (M.W.) of about 30,000 to about 1,000,000 Da.

6. The composition of claim 1, wherein the phosphate/acrylate co-polymer is a co-polymerized product of a mixture of acrylic acid, methacrylic acid, and 2-hydroxyethyl methacrylate phosphates of Formula 1 comprising acrylic acid in a molar percentage of 70-90%; methacrylic acid in a molar percentage of 5-20%, and hydroxyethyl methacrylate phosphates of Formula 1 in a molar percentage of 1-10%.

7. The composition of claim 1, wherein the phosphate/acrylate co-polymer is a co-polymerized product of a mixture of acrylic acid, methacrylic acid, and 2-hydroxyethyl methacrylate phosphates of Formula 1 comprising acrylic acid in a molar percentage of 80-90% or 85%; methacrylic acid in a molar percentage of 5-15% or 11%, and hydroxyethyl methacrylate phosphates of Formula 1 in a molar percentage of 2-6% or 4%.

8. The composition of claim 1. wherein the phosphate/acrylate copolymer is a random copolymer having a weight average molecular weight of 10,000 to 500,000, and the phosphate/acrylate copolymer is below its glass transition temperature.

9. The composition of claim 8, wherein the weight average molecular weight is 10,000 to 200,000 grams per mole, optionally, 10,000 to 40,000, 15,000 to 25,000, or 17,000 to 23,000 grams per mole.

10. The composition of claim 1, comprising a zinc salt, or a mono-, di- or trihydrate of a zinc salt.

11. The composition of claim 1, comprising at least one zinc salt chosen from zinc citrate trihydrate, zinc chloride, and zinc lactate.

12. The composition of claim 1, comprising a pyrophosphate salt.

13. The composition of claim 12, wherein the pyrophosphate salts are selected from the group consisting of tetrasodium pyrophosphate and tetrapotassium pyrophosphate.

14. The composition of claim 1, comprising:
phosphate/acrylate co-polymer in an amount of from 0.4% to 2.4%;
synthetic anionic linear polycarboxylates in an amount of from 0.01% to 2%;
a zinc salt in an amount of from 0.01% to 2%; and
one or more pyrophosphate salts in an aggregate amount of from 0.1% to 3%.

15. A method for the treatment and/or inhibition of a chemical stain, plaque, acid erosion, and/or tartar on a dental surface, comprising contacting the dental surface with a composition of claim 1.

16. A method for the treatment and/or inhibition of gum disease comprising contacting the oral cavity with a composition of claim 1.

17. A method for the treatment and/or inhibition of halitosis comprising contacting the oral cavity with a composition of claim 1.

18. A method for the inhibition of biofilm formation on a dental surface comprising contacting the oral cavity with a composition of claim 1.

* * * * *